United States Patent
Casparian

[11] Patent Number: 5,899,916
[45] Date of Patent: May 4, 1999

[54] DILATOR/HAIR IMPLANTOR DEVICE

[76] Inventor: Jacques Michael Casparian, 7711 Mohawk Dr., Prairie Village, Kans. 66208

[21] Appl. No.: 08/729,950

[22] Filed: Oct. 15, 1996

Related U.S. Application Data

[63] Continuation-in-part of application No. 08/392,107, Feb. 22, 1995, abandoned.

[51] Int. Cl.$^6$ .................................................. A61B 17/34
[52] U.S. Cl. .......................................................... 606/187
[58] Field of Search ................... 128/754; 606/187, 606/133, 184, 185, 167

[56] References Cited

U.S. PATENT DOCUMENTS

| | | | |
|---|---|---|---|
| 3,577,979 | 5/1971 | Van Der Gaast | 128/754 |
| 3,596,292 | 8/1971 | Erb | 606/187 |
| 4,004,592 | 1/1977 | Yamada . | |
| 4,160,453 | 7/1979 | Miller | 606/187 |
| 4,716,901 | 1/1988 | Jackson et al. | 606/185 |
| 4,751,927 | 6/1988 | Yamada . | |

FOREIGN PATENT DOCUMENTS

| | | | |
|---|---|---|---|
| 1953026 | 2/1972 | Germany | 606/187 |

*Primary Examiner*—Michael H. Thaler
*Attorney, Agent, or Firm*—Hovey, Williams, Timmons & Collins

[57] ABSTRACT

The present invention provides a dilator/hair implanter device comprising a wedge-shaped hollow body, said body having one end for engageably penetrating the scalp of a patient and wherein said body contains hair grafts for implantation into the scalp of said patient. Further provided is a dilator/hair implanter device comprising a body having at least two parts, said body having one end for engageably penetrating the scalp of a patient and wherein said body contains hair grafts for implantation into the scalp of said patient. Also provided are various methods of transplanting hair.

10 Claims, 3 Drawing Sheets

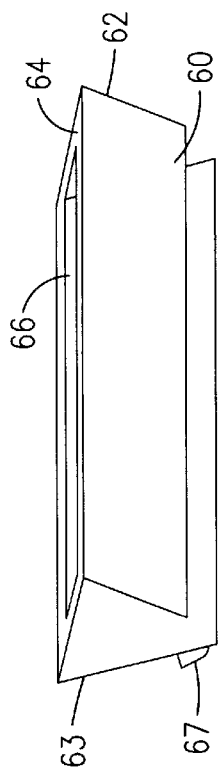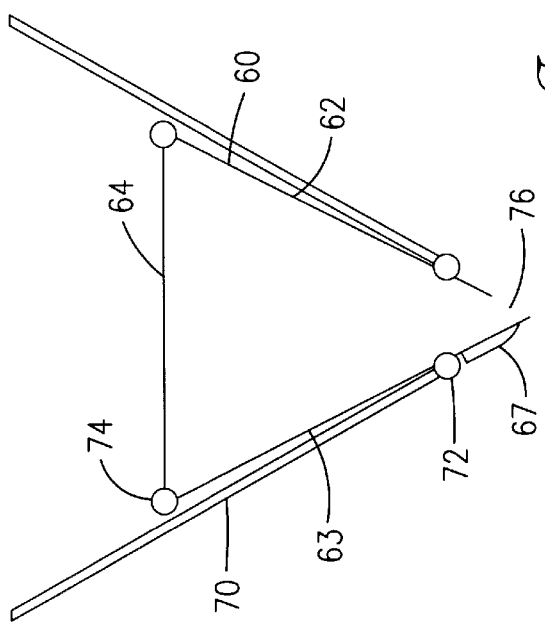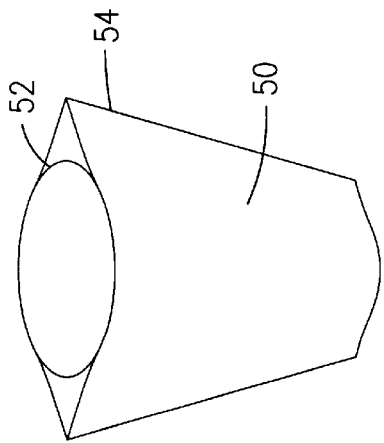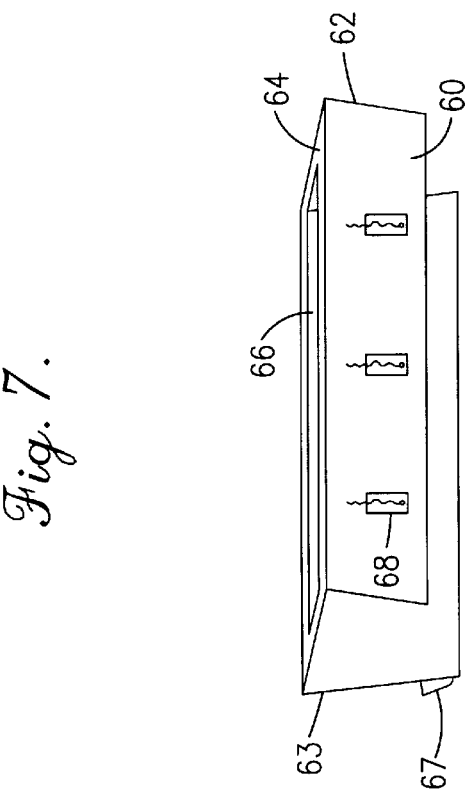

DILATOR/HAIR IMPLANTOR DEVICE

This application is a continuation-in-part of application Ser. No. 08/392,107, filed Feb. 22, 1995, now abandoned.

BACKGROUND OF THE INVENTION

1. Field of the Invention

The present invention relates generally to the fields of dermatologic surgery, hair transplantation and medical devices. More specifically, the present invention relates to a novel dilator/hair implantor device for use during hair transplantation procedures.

2. Description of the Related Art

Hair transplantation using hair grafts (standard, minigrafts and micrografts) has increased in popularity in recent years. The goal of hair transplantation using hairgrafts is to replace scarce or lost hair in one area of the scalp with hair taken from another area. Although numerous descriptions of techniques exist, the procedure is basically the same in most instances. Usually, the hair to be transplanted is taken from the back of the head where it is generally in abundance, even in those individuals with very thin or absent hair elsewhere. This is typically accomplished through removal of a relatively narrow strip of scalp from that area. As the resulting wound is likewise narrow, it can be closed by suturing. The resulting scar is minimal and the scar is generally well hidden by the surrounding hair. Many tiny hair grafts are then taken from the strip of scalp, using either a scalpel or a razor blade. These can be micrografts (1–3 hairs), minigrafts (usually 4–6 hairs) or standard grafts (up to 4 mm). These hair grafts are implanted into the desired area of the scalp, usually in front. Alternatively, hair grafts can be obtained by using a punch instrument (either manual or electric) which is a round cutting instrument, analogous to a cookie cutter, and excising hair grafts directly from hair bearing skin from the scalp or other hair-bearing regions of the body. These hair grafts can then be directly implanted as standard grafts or cut into smaller grafts, i.e., minigrafts or micrografts as desired. From this point on, the surgical techniques used varies.

There are 50 to 1,000 donor grafts per hair transplant session, which are implanted into an equal number of recipient sites. Before any hair graft can be transplanted, a small hole or opening into the scalp must be made. Recipient sites can be prepared with a variety of instruments: needles, small blades, or small punches. Appropriate size needles (to create microholes) or scalp blades (to create slits), as well as small skin punches (to create standard holes) have been used in the past by hair transplant surgeons.

Slits or microholes are typically placed between existing hair follicles or on the periphery of the scalp, performed with sharp scalpel blades or with 20, 18, 18 Nokor, or 16 Nokor needles. These slits or microholes are sometimes employed in individuals with earlier thinning or previous micrograft sessions. On the other hand, holes (1 mm to 4 mm in diameter) are sometimes used in individuals with starkly bald scalps or to remove bald skin from between plugs. However, the creation of holes, including the removal of bald scalp skin is more time consuming. Grafts generally are ejected, i.e., "pop out of the scalp" more easily from holes than from slits, but compression often results from grafting into slits. Some surgeons place a small notch at one end of the circle to alter the hole into an ellipse, sigma shaped or "q" shaped or place a second small slit, using a small blade, at an angle relative to the initial slit with the intention of greatly decreasing graft extrusion and compression. One may employ slits and holes in different recipient areas in the same patient, or in subsequent sessions in the same area. Hair graft insertion is typically performed using forceps or similar grasping instruments to take hold of the hair graft and push the graft into the recipient slit or hole while avoiding compression of the hair root.

After the cuts in the scalp have been made, some surgeons will then insert an instrument into the hole in order to dilate the hole, i.e., use a dilator. Examples of prior art dilators include small diameter solid metal tubes and wooden dowels. The objective when using a dilator is to facilitate placement of the hair graft which must be gently placed into the hole in the scalp. Microdilators, by expanding the size of recipient sites (holes, slits and microholes) facilitate micrograft placement, and can be helpful in some hands. Dilators are used to keep the donor slit or hole open, facilitate graft insertion by stretching the recipient site, act as markers for accurate spacing, aid in hemostasis, and prevent missed recipient sites and aid in quantifying the number of recipient sites prepared. However, because dilators involve two additional steps in hair transplantation, i.e., hair placement and removal prior to graft insertion, many surgeons find these extra steps time consuming.

Although surgeons have used dilators, it is time consuming for the hair transplantation surgeon to place the dilators into the scalp and then remove them. Although dilators save time during the actual placement of each graft into its recipient site, overall, the use of the dilators is viewed by many of those having ordinary skill in this art as taking more time than is desirable. Mainly for this reason, dilators are often omitted despite the above advantages.

Eberhard (German Patent No. 1,953,026) discloses a hair implantation device. Applicant's invention is an improvement over Eberhard by combining the necessary actions of cutting, dilating and inserting of the tissue into the scalp. Dilation is an important feature of tissue grafting to, e.g., minimize bleeding, ease the placement of grafts by making grafting faster and less traumatic, and prevent subsequent compression. The wedge design of Applicant's hairplanter is important for dilation and for gentle transfer, features not addressed and in some ways opposite of what Eberhard designed.

Applicant's device facilitates a gentle transfer of the hair follicle not necessary with artificial hairs, with efforts to minimize vertical and lateral forces through employment of Applicant's wedge design so at to dilate the recipient site and facilitate a gentle sliding implantation of graft. By contrast, Eberhard's claims relate to foreign/artificial hair that has different handling and physical requirements. This is illustrated clearly by the impaling of the artificial graft which is an integral feature of technique of transplantation disclosed in Eberhard and the anchor that has no biological counterpart for tissue transfer. Moreover, Applicant's device is not limited structurally to a cylindrically symmetric device like the needle/cannula system disclosed by Eberhard.

The actual insertion or placement of the hair grafts into the scalp hole or slit is the most difficult and important part of hair transplant surgery. The prior art is deficient in the lack of simple, cost-effective means of dilating hair graft sites and easily inserting hair grafts during hair transplant surgery. The present invention fulfills this longstanding need and desire in the art.

SUMMARY OF THE INVENTION

In one embodiment of the present invention, there is provided article of manufacture comprising a dilator/hair implanter device comprising a non-cylindrical wedge-shaped hollow body, said body having one end having an opening for engageably penetrating a patient's scalp, wherein said body has a length of from about 10 mm to about 200 mm, a minimum width up to about 4.5 mm and wherein said body has at least one fin-like element to facilitate dilation of the implant, said element extending to within about 0.7 cm of the end of said body that penetrates the scalp. In one embodiment, this wedge is transected or semi-conical in its configuration.

In another embodiment of the present invention, there is provided a dilator/hair implanter device comprising a non-cylindrical body having at least two wedges, said body having one end for penetrating a patient's scalp, wherein said body of each wedge has a length of from about 10 mm to about 200 mm, a width minimum of up to about 4.5 mm and wherein said body has at least one fin-like element attached to the distal end of at least one wedge, said fin-like element extending to within about 0.7 cm of the end which penetrates the scalp.

In still yet another embodiment of the present invention, there is provided a method of implanting hair grafts into the scalp of a human, comprising the steps of: placing one or more hair grafts onto the hair transplanter of the present invention; engaging said scalp with said transplanter so as to create and dilate a hole within which to place said graft; and inserting said graft into said hole.

In still yet another embodiment of the present invention, there is provided a dilator/hair implanter device comprising a wedge-shaped hollow body, said body having an inclined plane or inclined surface in its interior aspect and having in one end an opening for engageably penetrating a patient's scalp, wherein said body has a length of from about 10 mm to about 200 mm, a minimum width of up to about 4.5 mm and wherein said body has at least one fin-like element attached to the proximal end of said body, said fin-like element extending to within about 0.7 cm of the end which penetrates the scalp.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 1 shows one embodiment of the dilator/hair implantor device of the present invention.

FIG. 2 shows another embodiment of the dilator/hair implantor device of the present invention in which the body of the device is comprised of two separate semi-conical halves.

FIG. 7 shows a hollow wedge embodiment 50 consisting of an ellipse 52, with laterally oriented and outwardly directed fin elements 54.

FIG. 8 shows a hollow wedge embodiment 60 consisting of a polygon 62 with lateral faces 62 and 63 and a top surface 64, having a longitudinal opening 66 and a fin element 67.

FIG. 9 shows the polygonal wedge shaped embodiment with hair grafts 68 in place.

FIG. 10 shows the side view of the polygon with an opening tip 76 to which are attached the lever arms 70 at the fulcrums 72. When the lever arms are pushed towards one another, fulcrums 74 are utilized to enable spreading of the sides 62 and 63.

DETAILED DESCRIPTION OF THE INVENTION

Figure 1A:
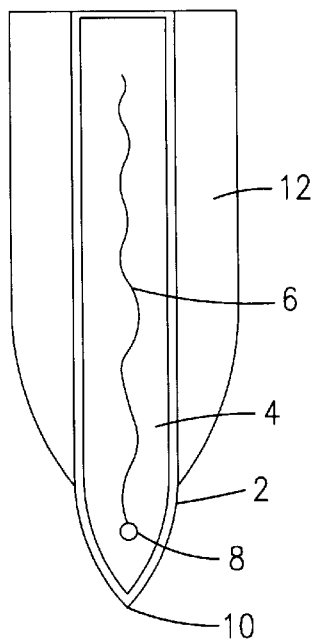
FIG. 1A shows an embodiment of the dilator/hair implantor device having short fins.

There are many structural and functional differences between the devices of the present invention and the device disclosed by Eberhard. Functionally, the exterior of Applicant's device can be a wedge in a vertical orientation (e.g., a cone) or a polygonal wedge when viewed from above (i.e., in horizontal cross sectioning) thereby enhancing dilatation during implantation and spreading. In contrast, Eberhard's claim 4 teaches spreading the device only wide enough to permit the insertion. Eberhard's claim 6 teaches limiting the diameter of the cannula to minimize dilatation while claim 9 teaches arc shaped spreaders as opposed to wedge shaped designs, including fins. In fact, all but the absolutely minimum dilation may be undesirable for artificial hairs because it may result in the hairs falling out as suggested by Eberhard's claim 6. In contrast, Applicant's device and methods can be utilized to maximize dilatation.

Eberhard's claim 4 relates to an impaling with the anchor using axial forces listed in Eberhard claim 2 that the anchor goes below the points of the needles. This is neither possible nor desirable in tissue transplantation. In contrast, the hollow wedge design of Applicant's device serves to diminish the vertical axis forces, i.e., the opposite goal Eberhard.

Eberhard does not disclose fins that are equivalent in structure and function to the fins on Applicant's device. Eberhard's claims do not teach a fin that impales the scalp but rather a mechanical limiting device in association with an adjusting device. In contrast, Applicant's fins are of a different structure for a completely different function, i.e., dilating the recipient site of the hair graft, or to be mechanically limiting by the fin coming in contact with the skin.

The current device utilizes not just vertical vectors but also horizontal ones in the non-obvious utilization of a hollow wedge. This design combines the features of improved loading and unloading of the tissue graft, through a wedge shaped hollow interior. The inclined plane or inclined surface design of the interior of a hollow wedge would facilitate not only tissue being placed into the device, but also its being deposited into the scalp, acting as a chute at both ends. Inclined surface refers to an inclined plane but generalized to account for sloping, curved surfaces such as the interior of a hollow cone. Additionally, the exterior wedge of the present design mechanically stretches the surrounding recipient tissue to minimize the compression of the graft (just the opposite of the intent of the artificial hair device which seeks to maximize the lateral pressure holding the thread in place). As a result, less vertical pressure is applied as the biological tissue is inserted into the device and gently pushed down to its recipient site. Furthermore, Applicant's device with slits or a device in several parts makes a channel wide enough so that a graft can possibly inserted. In combination with one or more levers, fins, or rods that facilitate spreading, Applicant's device creates a wide recipient site to minimize the vertical forces needed to transfer the graft to the desired location.

The device of the present invention serves to dilate the donor recipient site and implant the hair graft into the donor holes simultaneously. Because of its dual action, and ease of use, this device enhances the efficiency of hair transplant procedures using all types of grafts, including standard grafts, and especially mini-grafts and micro-grafts. This device reduces the trauma of implanting the hair grafts, and ensures that these grafts are properly oriented (compared with the conventional technique where the shafts may be implanted at undesirable angles). Leaving all of these dilator/implanters in place until all of the 50 to 1,000 grafts are transferred facilitates the transplant procedure since there is less chance of skipping over holes that were created or placing two grafts in any one site. Furthermore, this device would reduce the chance that the initial grafts placed during a transplant session would be subsequently ejected from recipient holes while new grafts are being placed into adjacent holes (which commonly occurs during conventional implantation as the new grafts being pushed into undilated holes exert significant lateral and upward stretching forces on adjacent scalp skin).

Other advantages of the dilator/hair implantor of the present invention include enabling more grafts to be done during each transplant session, since this device will enable the rate-limiting step of implantation to be more efficient, as compared with merely using forceps. Also, the enhanced orientation gained by this device enables longer hairs, rather than hair shafts that are only two to four millimeters above the skin as are currently used, to be transplanted. This would give the individual a more natural appearance immediately following a hair transplant session. Additionally, this device could potentially enhance the proportion of "graft takes", diminish trauma to the hair graft associated with the use of forceps or similar pushing instruments, diminish compression effects found after grafting procedures, and minimize the number of improperly oriented hairs that can lead to pseudo-folliculitis. None of the prior art tools used to implant hairs have the combined functions of the dilator/hair implantor device of the present invention.

In one embodiment, the dilator/hair implantor device of the present invention works on the principles of using a wedge (the exterior surface) to serve as a dilator, and an inclined plane (the interior surface) for the implantation. Each graft uses one hair transplant dilator/implanter. In one embodiment, there is a thin cone (wedge) which has had a plane section removed at an angle relative to its long axis. Thus, hair grafts can be directly placed into the hollow "conical tube" (the inclined plane). The hair graft is placed into this conical tube at the tip of the transected cone with the subcutaneous tissue (lowest part of the graft) at the bottom and the top oriented towards the cone's base. As a wedge, the cone is placed into the scalp recipient site with the tip down into the recipient scalp (slit or hole) as a dilator, with the base projecting out of the scalp, serving as an easy marker that a hair has been transferred to the scalp recipient site.

There are advantages to leaving each dilator/hair implanter device in place until all 50 to 1,000+ grafts have been introduced into the scalp. For example, the dilator/hair implanter of the present invention ensures a one to one correlation between recipient holes and grafts, and minimizing the "ejection" phenomena described above. Then, after all of the dilator/hair implanters have been placed, the surgeon applies gentle pressure to the top of the graft, while pulling the dilator/implanter out of the scalp. As each dilator/implanter is removed, there is a sliding "inclined plane" or inclined surface effect between the dilator and the graft facilitating the device's removal, which completes the implantation of the grafts.

These dilator/implanters are easily made in different sizes according to the size of the graft being implanted (one hair to 4.5 millimeter grafts). Additionally, to impede the dilator/implanter from rolling, e.g., on a table while the graft is being placed into it, there are edges on the outside of the cone towards its base, i.e., the part that does not enter the scalp. Furthermore, the dilator/hair implanter device, is described in another embodiment, in which a blade like "fin or fins" are added to the cone near its tip to make a slit (or slits) adjacent to the cone as it is introduced into a hole. In one embodiment, the fins are triangular wedges having their base attached to the side of the device and the tip projected radially outward. This modification of the device saves the additional step of creating "small slit or slits" discussed above. The tip of the transected cone may be sharpened, so that instead of being introduced into a slit or hole, the dilator/implanter could also be pushed into an area of intact scalp to create a microhole (or series of slits in combination with the fins) into which it would slide into place to dilate the slit(s) and implant the hair graft. While the dilator/hair implanter of the present invention adequately serves the desired functions listed above, a person having ordinary skill in this art would readily be able to make certain refinements, including determining the optimal dimensions of these transected cones as well as which materials should be used (i.e. metal vs. plastic) to optimize the practicality, usefulness, and affordability of the dilator/hair implanter of the present invention.

A grafting session in a hair transplantation surgery involves the preparation and placement of hundreds of grafts. Thus, the value of eliminating any unnecessary steps is important and easily appreciated by a person having ordinary skill in this art, i.e., generally, a dermatalogic or plastic surgeon. The present invention allows the hair transplant surgeon to make a hole, dilate the hole and subsequently place the graft with a minimum of movements. Furthermore, the present invention provides the transplant surgeon with an crucial measure of control over the angle of insertion of the hair follicle(s). Control over the angle of insertion of the hair follicle is important to the proper execution of the hair transplant surgical procedure and such control is mainly lacking in the prior art devices.

Another embodiment of the device utilizes the inclined plane or surface (since with curved interior surfaces, there may be no plane surface, per se, but the equivalent for curved surfaces) for the interior of a hollow wedge to improve the ease of loading hair grafts into the device. Many practitioners place the individual hair grafts (micrografts, minigrafts, and standard grafts) unto a substance such as TELFA® which has a surface to which they are mildly adhesive to facilitate handling of the grafts. One advantage of these surfaces is that they enable one or several hair grafts to be picked up and placed on the back of the hand in the proper orientation, facilitating their handling. Typically, these grafts are then picked up by forceps (having to be extremely gentle in the transfer process so as not to exert pressure on the hair producing portion of the follicles) and placed into the recipient site. Alternatively, if a needle or cylinder is used for implantation, the grafts are placed either on the top, or side of the needle that has a slot, or loaded by being pushed backwards into the orifice through which they will emerge.

However, needles are by definition slender devices, and are not designed to be wider beyond the distal most portion of the device, often having a constant diameter (with merely a distal bevel) or being tapered only for the distal most 1–3 mm. The narrow diameter of a needle has the undesirable effect of making loading of the graft into the device either from the bottom of a needle into its tiny orifice side (if there is a long bevel or slot) or from the top difficult, and often necessitating a separate element, such as a funnel. However, in this embodiment, the inclined plane of the interior of a hollow wedge enables a bigger recipient site for inserting the graft into the device, either from the side by adding a longitudinal slot, or else by inserting directly into the top, compared with the diameter of the needle insertion portion (i.e. the distal approximately 0.6 cm).

One embodiment of the present invention has an opening or longitudinal slot that may of may not be in continuity with the orifice at the end of the device that enters the scalp. This opening is made wide enough to allow easy insertion of the hair graft into the device. One way of doing this is to utilize an inclined plane or inclined surface on the interior of the device, typically with widening of the interior width being accompanied by some degree if not proportional widening of the exterior width as well, with the widening not just at the distal tip that gets inserted into the scalp (approximately 6 mm), if tapering is desired at this portion of the device, but more proximally as well towards the other end, so that the width of the interior increases to at least 1.2 to 2 or more times the width of the device at the proximal most portion of insertion of the device (i.e. about 6 mm). Clearly, a virtual unlimited widening occurs, depending only upon the average angle of the inclined surfaces and the length of the device. Wider interiors facilitate not only ease of insertion of single grafts, but also multiple grafts, or needles or cylinders containing grafts with the device or blades or needles to create holes, with these latter embodiments having the device acting as a sheath (vide infra).

Clearly an inclined surface facilitates top loading of the grafts. Additionally, a longitudinal fissure, slot, or opening can then be created with a width at least as wide, if not up to several times wider than the width of the device as it is when it is inserted into the scalp (i.e., if the width of the interior of the device was 1.5 times the width of the proximal most portion of the inserted distal portion of the device, which can be arbitrarily called 1 mm) then if the opening consisted of one-half of the surface of the device being removed to hemisection to device in creating the slot, then the interior portion of the opening would be 1.5 mm. If the opening were made by removing 90 degrees of the surface, then the interior width would be the square root of two times 0.75 mm, for this example, with lesser angles would have a smaller opening width, while angles greater than 90 but less than 180 being wider opening widths. These wide openings would facilitate a much easier insertion of the graft (or grafts) as it is being placed into the device, as compared with trying to squeeze it into a narrow channel or orifice. Furthermore, if a wedge of fin is placed on at least one edge of the slot (top, sides or bottom), the wedge or fin can facilitate graft insertion, not only with forceps (where the graft can more easily be pushed into the slot) but particularly with another method of graft insertion involving surfaces to which it adheres. In this method, a hair graft is placed on a TELFA® or other surface to which it mildly adheres. The TELFA® or other surface and graft are then gently pushed over the wedge or fin at the edge of a slot in such a way that the graft is separated from the surface (analogous to peeling the graft from an adhesive backing), and therefore easily loading the graft (or grafts) into the device.

The advantage of having a slot contiguous with the opening is that it allows a groove by which a device such as a narrow wedge can push the graft all of the way down the device to the distal end of the device which may be transcected or beveled, with the graft being held down in the appropriate place on the recipient site while the device is pulled out or extracted from the skin.

As indicated before, there are advantages to having different shaped hollow wedges for different shaped and sized donor grafts and recipient sites, including cone shaped, elliptical, and polygonal. Additionally, the presence of fins can be advantageous not only in loading hair grafts into the device at the border of one of the edges of the slot or slots, but also in cutting, dilating, etc. As noted above, hard steel and plastics have can be utilized for the device. However, the device can also have flexible material, such that if there is a plunger used which is either rigid or has a degree of elasticity which is the size of the interior of the device proximally, as it goes towards the distal end of the device while pushing on the interior walls of the device, the device becomes further dilated as the plunger acts as a wedge to expand the interior of the device. Dilation can also be achieved by having the slot having a wedge shape with a component of the slot narrowing as it approaches the distal tip (i.e. the end that enters the scalp), such that as a wedge that is the width of the opening proximally is pushed down distally. Furthermore, the presence of two or more longitudinal slots can enable a pushing wedge (i.e. a needle tip) to be inserted through the entire width of the device out the other side, enabling a greater degree of dilation as the pushing wedge is brought down towards the distal tip as the graft is being pushed down.

There are settings in which the hollow wedge is utilized after a recipient site is made either by slits or holes or some combination of these. As noted previously, the creation of side slits for holes or slits can be extremely valuable, albeit time consuming, in preventing compression and facilitating dilation. However, a hollow or non-hollow wedge with fins can be initially inserted, thereby creating the desired recipient site (i.e., the wedge can be of a solid (or hollow) needle design (like an 18 gauge needle, for example) that then has a side fin that extends far enough to the tip of the needle that engagebly penetrates the scalp so that a hole with a side slit is created as it is inserted. If the needle is hollow, this could then serve as an implanting device as well, particularly if there is an inclined surface with widening of the diameter of the device to facilitate insertion of the grafts.

The present invention is also directed to a dilator/hair implanter device comprising a non-cylindrical wedge-shaped hollow body, said body having one end having an opening for engageably penetrating a patient's scalp, wherein said body has a length of from about 10 mm to about 200 mm, a minimum width up to about 4.5 mm and wherein said body has at least one fin-like element to facilitate dilation of the implant, said element extending to within about 0.7 cm of the end of said body that penetrates the scalp. Preferably, the body is composed of a material selected from the group consisting of stainless steel and hard plastic. Flexible materials such as flexible steel can also enhance dilation. Generally, the end having an opening for engageably penetrating a patient's scalp has a sharp edge.

The present invention is also directed to a dilator/hair implanter device comprising a non-cylindrical body having at least two wedges, said body having one end for engageably penetrating a patient's scalp, wherein said body of each wedge has a length of from about 10 mm to about 200 mm, a width minimum of up to about 4.5 mm and wherein said body has at least one fin-like element attached to the distal end of at least one wedge to facilitate dilation of the implant, said fin-like element extending to within about 0.7 cm of the proximal end of said wedge. Preferably, the body is composed of a material selected from the group consisting of stainless steel and hard plastic but other embodiments could use flexible materials such as flexible steel. In one embodiment, the dilator/hair implanter device has a lever attached to each part of said body. Preferably, the lever is selected from the group consisting of a compound $3^{rd}$ class lever, a compound $1^{st}$ class lever, compound $1^{st}$ class lever having a spring, a first class lever having separate fulcrums or a compound $1^{st}$ class lever attached to a compound $3^{rd}$ class lever.

The present invention is also directed to a method of implanting hair grafts into the scalp of a human, comprising the steps of: placing at least one hair graft onto the dilator/hair implanter device of the present invention; engaging said scalp with said dilator/hair implanter device so as to create and dilate a hole within which to place said graft; and inserting said graft into said hole. Preferably, in one embodiment, the hair grafts are single hair grafts. It is also specifically contemplated that one could use and place in the transplanter various type of hair grafts, i.e., multiple groups or units of grafts taken from the donor area of the scalp at one time, such as a row of hairs that could be inserted simultaneously.

The present invention is also directed to a dilator/hair implanter device comprising a wedge-shaped hollow body, said body has a length of from about 10 mm to about 200 mm, and a minimum width of up to about 4.5 mm and said body has an opening for penetrating a patient's scalp; and wherein said body has at least one lengthwise slot, said slot having a maximal width wider than the interior width of the device at a distance of 0.6 cm from the tip of the device at the end which penetrates the scalp. Preferably, the hollow body has a shape selected from the group consisting of cone shaped, elliptical, and polygonal and has an interior width that increases in diameter from the end of the body that penetrates the scalp. In one embodiment, the lengthwise slot is contiguous with the opening of the body. Preferably, the maximum width of the interior of the body is at least 1.5 times the interior width of the body compared with the interior width at a distance of 0.6 cm from the tip of which penetrates the patient's scalp. In a preferred embodiment, the body has one or more fins. Preferably, the body is made from a material selected from the group consisting of semi-hard plastic, hard plastic, flexible steel and hard steel. In one embodiment, the slot has one or more fins attached to an edge of the slot. In another embodiment, the slot has one or more edges having a wedge shape.

The following examples are given for the purpose of illustrating various embodiments of the invention and are not meant to limit the present invention in any fashion.

EXAMPLE 1

The dilator/hair implanter of the present invention allows the transplant surgeon to: 1) make a hole in the scalp where the graft is to be placed, 2) dilate the hole; 3) insert the graft into the dilator/hair implanter of the present invention; and 4) manipulate the graft, with the tip of a jeweler's forceps or other small instrument, down the device into the scalp. The device is then withdrawn while the graft is held in place. Following withdrawal, the graft should be in its proper position.

Figure 1B:
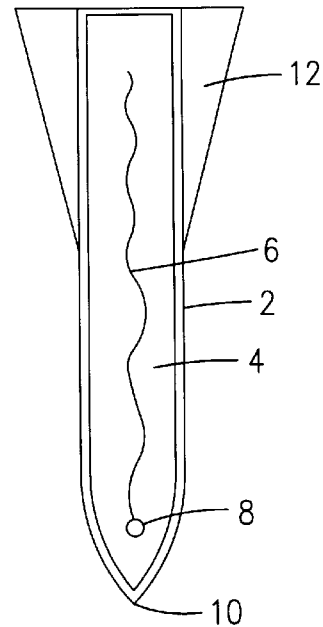
FIG. 1B shows an embodiment of the dilator/hair implantor device having longer fins.

FIG. 1 depicts one embodiment of the dilator/hair implanter of the present invention. With reference now to FIG. 1, there is shown a dilator/hair implanter 2 comprised of a semi-conical, mainly hollow body 4. The conical body 4 contains hair shaft 6 having a hair root(s) 8. The semi-conical body 4 ends in an extremely sharp tip 10. Further, the semi-cylindrical body 4 may have a side "fin-like" element (s) 12. The "fin-like" element 12 may extend from the top of body 4 to the tip 10. It is specifically contemplated that the "fin-like" element would be very sharp so as to allow the surgeon to use the lower aspect of the "fin" to dilate the recipient site.

Figure 2A:
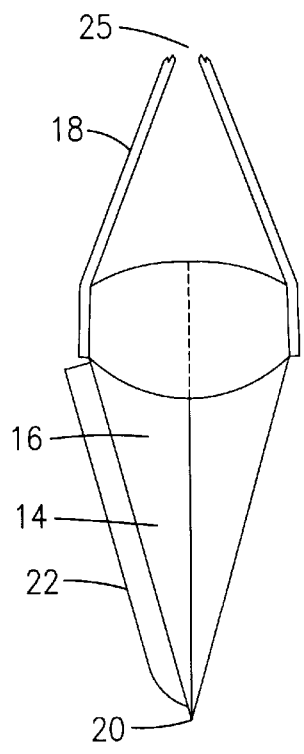
FIG. 2A shows the dilator/hair implantor device in the closed position.

FIG. 2 illustrates another embodiment of the dilator/hair implanter of the present invention in both open and closed variations. With reference now to FIG. 2A, there is shown a dilator/hair implanter 14 comprised of a semi-conical, mainly hollow pair of half-bodies 16. The half-body 16 has a "lever" 18 attached to the upper aspects of the body 16. This dilator/hair implanter also ends in a sharp tip 20 and has a side "fin-like" element 22. The "fin-like" element 12 may extend from the top of body 14 to the tip 20 and the half-body 16 may have more than one "fin" 22. It is again specifically contemplated that the "fin-like" element would be very sharp so as to allow the surgeon to use the lower aspect of the "fin" to dilate the recipient site.

Figure 2B:
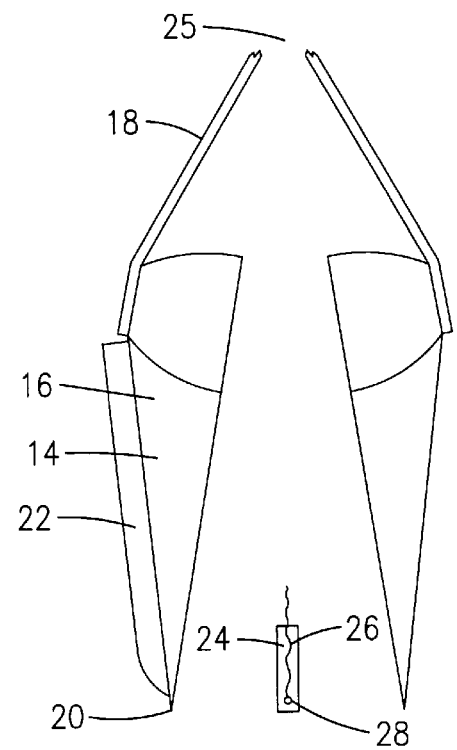
FIG. 2B shows the dilator/hair implantor device in the open position.

FIG. 2B shows an embodiment of the dilator/hair implanter of the present invention in an open configuration. Shown inside the two semi-conical half-bodies is a hair graft 24 comprising a hair shaft 26 having a hair root 28.

Essentially, the working nature of this embodiment of the dilator/hair implanter of the present invention is as follows. Using the embodiment of the implanter depicted in FIG. 1, a hair graft is inserted into the cone so that the roots of the graft are towards the tip and the base of the shaft is towards the base. This placement of the graft is performed through the base using the hollow inside as a chute or else the transected tip. After the device is inserted into the intact scalp (with a sharp tip and/or fins) or slit or hole, the hair graft slides along the hollow inside (incline plane or inclined surface) as the device is pulled out of the scalp. To facilitate the hair graft remaining in the scalp, the graft is held down in the scalp, instead of being forced down as in the prior art techniques such as when using forceps, a cotton tip applicator, etc.

For the embodiment of the dilator/hair implanter of the present invention depicted in FIG. 2, a surgeon places a hair graft into one part of the semi-cone so that the graft rests on the hollow part with the root towards the tip and the top of the hair shaft laying towards the base by being in an open position. Insertion of the graft into the dilator/hair implanter of the present invention is facilitated. Next, the device is changed to a closed position and inserted into the scalp as described above. Following insertion, the device can be changed to an open position enhancing dilation of the recipient site as well as facilitating removal of the device, completing the implantation of the hair graft. The hair graft is held down in the scalp using forceps, a cotton tip applicator, etc.

The hair grafts may be placed in the body 4 of the dilator/hair implanter 2 either before or after insertion of the dilator/hair implanter 2 into the patient's scalp. Indeed, it is contemplated that a hair transplant surgeon may well desire to load the single hair grafts in the body 4 prior to insertion of the tip 8. In fact, one may desire to load multiple hair grafts, i.e., "stack" the hair grafts onto the dilator/hair implanter 2 prior to insertion of the tip 8.

With reference to FIGS. 1 and 2, the body 4 of the dilator/hair implanter 2 may be composed of a variety of materials. For example, the body 4 is fashioned from a stainless steel, such as a stainless steel needle. It is also contemplated that the body 4 may be composed of other suitable materials, e.g., hard plastics.

Generally, the size of the body 4 of the dilator/hair implanter 2 is approximately 18–20 gauge, at an approximate minimum. Thus, the length of the body 4 of the dilator/hair implanter 2 is preferably from about 10 mm to about 40 mm. Further, the width of the body 4, i.e., the diameter of the dilator/hair implanter of the present invention is from about 0.4 mm to about 4.5 mm. Within said semi-conical body 4, it is contemplated that no more than approximately 270° of the what would have been the total cylinder was removed. Furthermore, the width of the "fin" 12 in FIG. 1 or "fin" 22 in FIG. 2A would be from about 0.01 mm to about 1.5 mm. Generally, the length of the fin 12 in FIG. 1 or "fin" 22 in FIG. 2A would be from about 3 mm to about 40 mm.

The lever 18 of the dilator/hair implanter device of the present invention can be selected from a wide variety of levers well known to those of ordinary skill in this art. Representative example of suitable lever attachments include a compound $3^{rd}$ class lever, a compound $1^{st}$ class lever, compound $1^{st}$ class lever having a spring, two first class levers having separate fulcrums that are connected or two $1^{st}$ class levers joined by a compound $3^{rd}$ class lever which could have a spring at the fulcrum analogous to a tea bag holder. It is further contemplated that one with ordinary skill may desire the advantage of placing a hook to lock the levers into a closed or open position A person having ordinary skill in this art would readily be able to substitute one class of lever for another for use in the dilator/hair implanter device of the present invention and be able to achieve essentially the same results. Besides enhanced precision and mechanical advantages that these levers provide, they also facilitate loading hair grafts, dilitation of the recipient sites and removal of the device to complete implantation.

The dilator/hair implanter device of the present invention can be used in conjunction with other hair transplantation devices. For example, a person having ordinary skill in this art would readily recognize that various injector or injection means may be utilized in conjunction with the dilator/hair implanter of the present invention.

In yet another embodiment of the present invention, the cone of claim 1 is made with a fissue along its long axis. This embodiment is made of stainless stell having a suitable degree of elasticity. The device would have two positions, one closed, in practical form identical to the device described by claim 1, except having a fissure from one end to the other longitudinally; and the other form open, representing a relaxed state of the elastic material. The open position would facilitate loading of the hair graft into the device and removal of the device from the scalp following graft placement, analogous to the devided cone of claim 10 in an open position. Through pressing on the sides and possibly locking the device with a washer at the base, the device is changed to a closed position and inserted into the scalp (bald or at recipient holes or slits. It is then changed to the open position, i.e., through removal of the washer, thus facilitating removal of the device. In addition to facilitating the final implantation stage, the device having levers enhances dilitation of the scalp recipient sites.

The device of the present invention may have razor sharp surfaces throughout all of the exposed edges except the base, i.e., the tip and sides. This enables one to cut off the hair grafts from the hair strip and allows simple loading of the grafts into the device.

Alternatively, the devices of the present invention could harvest grafts directly from donor sites on the scalp, i.e., intact scalp or other hair bearing skin, e.g., previously transplanted sites, by being impaled in the skin, cut out a plug and then transplanting this graft.

Alternatively, the hollow wedge can have other configurations besides being conical including a modified cone which is elliptical rather than round in cross section. An alternate configuration is a cone that is polygonal in cross section, somewhat analogous to a pymamid or in horizontal in cross section similar to a wedge shaped paper holder. Furthermore, it is appreciated by those having ordinary skill in this art that the inner surface of the semi-cone, divided semi-cone or wedge may have foci of altered surfaces or tooth-like projections that would facilitate holding the graft (s) in the device of the present invention and/or its release. Furthermore, these devices described herein may be connected to one another so that many hair implantation devices are inserted into the scalp simultaneously.

Figure 3:
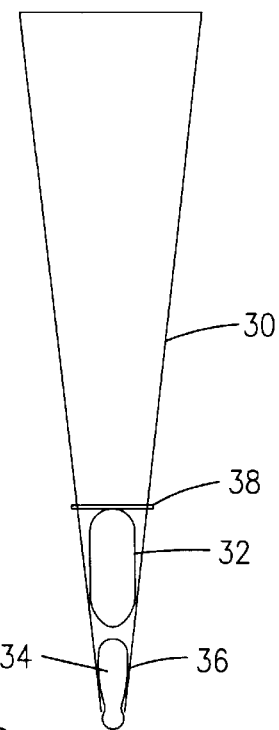
FIG. 3 shows another embodiment of the present invention comprising a body having at least one lengthwise slot, or alternatively or additionally, a first lengthwise slot.
Figure 4:
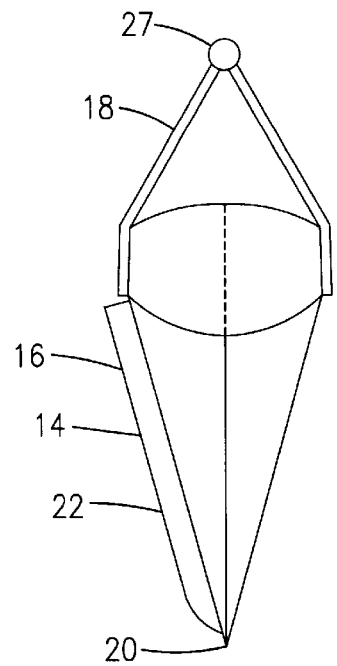
FIG. 4 shows two wedges with a compound third class lever (with a fulcrum 27).
Figure 5:
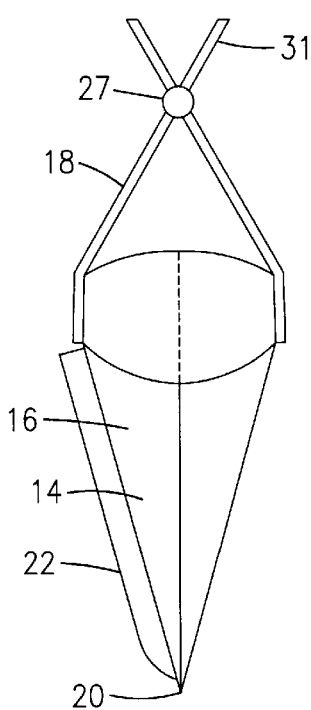
FIG. 5 shows two wedges with a compound first class lever with lever arms 18 leading to a fulcrum 27 and extending level arms 31.
Figure 6:
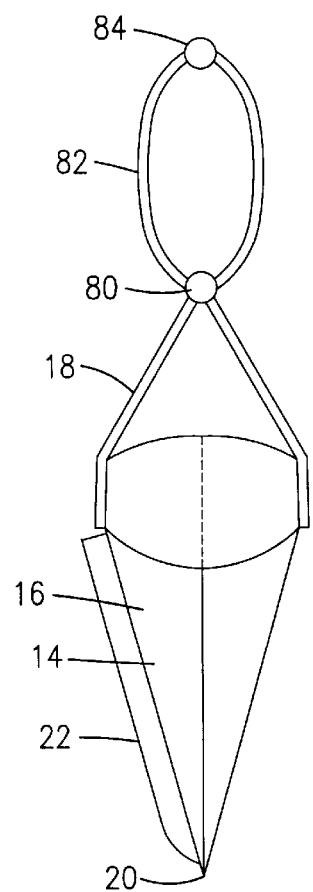
FIG. 6 shows two wedges with a third class lever (with a fulcrum 84 connected to lever arms 82 that meet at a fulcrum 80 connected with level arms 18.

FIG. 3 shows another embodiment of the present invention comprising a body 30 having at least one lengthwise slot 32, or alternatively or additionally, a first lengthwise slot 34 which is contiguous with the end of the body which penetrates the scalp. Further contemplated is that the body 30 may have either a fin 36 oriented vertically or a fin 38 oriented horizontally.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with any methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A dilator/hair implanter device comprising a non-cylindrical wedge-shaped hollow body, said body having one end having an opening for penetrating a patient's scalp, wherein said body has a length of from about 10 mm to about 200 mm, a minimum width up to about 4.5 mm and wherein said body has at least one outwardly directed, non-arcuate shaped, laterally oriented fin-like element, said element extending to within about 0.7 cm of the end of said body that penetrates the scalp.

2. The dilator/hair implanter device of claim 1, wherein said body is composed of a material selected from the group consisting of stainless steel and hard plastic.

3. The dilator/hair implanter device of claim 1, wherein said end having an opening for engageably penetrating a patient's scalp has a sharp edge.

4. A method of implanting hair grafts into the scalp of a human, comprising the steps of:
   placing at least one hair graft onto the dilator/hair implanter device of claim 1;
   engaging said scalp with said dilator/hair implanter device so as to create and dilate a hole within which to place said graft; and
   inserting said graft into said hole.

5. A dilator/hair implanter device comprising a non-cylindrical body having at least two wedges, said body having one end for penetrating a patient's scalp, wherein said body of each wedge has a length of from about 10 mm to about 200 mm, a width minimum of up to about 4.5 mm and wherein said body has at least one outwardly directed, non-arcuate shaped, laterally oriented fin-like element attached to at least one wedge, said fin-like element extending to within about 0.7 cm of the end of said body that penetrates the scalp.

6. The dilator/hair implanter device of claim 5, further comprising a lever attached to at least two wedges of said body.

7. The dilator/hair implanter device of claim 5, wherein said lever is selected from the group consisting of a compound $3^{rd}$ class lever, a compound $1^{st}$ class lever and a compound $1^{st}$ class lever having a spring.

8. The dilator/hair implanter device of claim 5, wherein said body is composed of a material selected from the group consisting of stainless steel and hard plastic.

9. A method of implanting multiple hair grafts into the scalp of a human, comprising the steps of:
   placing at least one hair graft onto the hair transplanter of claim 4;
   engaging said scalp with said transplanter so as to create and dilate a hole within which to place said grafts; and
   inserting said grafts into said hole.

10. A dilator/hair implanter device comprising a wedge-shaped hollow body, said body has a length of from about 10 mm to about 200 mm, and a minimum width of up to about 4.5 mm and said body has an opening for penetrating a patient's scalp; and
   wherein said body has at least one lengthwise slot, said slot having a maximal width wider than the interior width of the device at a distance of 0.6 cm from the tip of the device at the end which penetrates the scalp and wherein the maximum width of the interior of the body is at least 1.5 times the interior width of the body compared with the interior width at a distance of 0.6 cm from the tip of which penetrates the patient's scalp and wherein the body has one or more outwardly directed, non-arcuate shaped, laterally oriented fins.

* * * * *